United States Patent [19]

Mederski et al.

[11] Patent Number: 5,532,276

[45] Date of Patent: *Jul. 2, 1996

[54] IMIDAZOPYRIDINES

[75] Inventors: Werner Mederski, Erzhausen; Dieter Dorsch, Ober-Ramstadt; Mathias Osswald, Zwingenberg; Norbert Beier, Reinheim; Pierre Schelling, Muhltal; Klaus-Otto Minck, Ober-Ramstadt; Ingeborg Lues, Darmstadt, all of Germany

[73] Assignee: Merck Patent Gesellschaft mit beschrankter Haftung, Darmstadt, Germany

[ * ] Notice: The term of this patent shall not extend beyond the expiration date of Pat. No. 5,242,928.

[21] Appl. No.: 353,309

[22] Filed: Dec. 5, 1994

[30] Foreign Application Priority Data

Dec. 6, 1993 [DE] Germany ............ 43 41 453.2

[51] Int. Cl.⁶ .................. A61K 31/435; C07D 471/04
[52] U.S. Cl. ........................... 514/303; 546/118
[58] Field of Search ................ 514/303; 546/118

[56] References Cited

U.S. PATENT DOCUMENTS

| | | | |
|---|---|---|---|
| 5,036,049 | 7/1991 | Watkins | 514/16 |
| 5,242,928 | 9/1993 | Mederski et al. | 514/303 |
| 5,321,137 | 6/1994 | Mederski et al. | 546/308 |
| 5,332,750 | 7/1994 | Mederski et al. | 514/340 |
| 5,371,226 | 12/1994 | Mederski et al. | 546/156 |
| 5,389,642 | 2/1995 | Dorsch et al. | 514/303 |

FOREIGN PATENT DOCUMENTS

| | | |
|---|---|---|
| 0400974 | 12/1990 | European Pat. Off. . |
| 0505893 | 9/1992 | European Pat. Off. . |
| 0547514 | 6/1993 | European Pat. Off. . |
| 0564960 | 10/1993 | European Pat. Off. . |
| 0574846 | 12/1993 | European Pat. Off. . |

OTHER PUBLICATIONS

The Merck Manual of Diagnosis and Therapy. Eleventh Edition (1966) p. 472.

*Primary Examiner*—C. Warren Ivy
*Assistant Examiner*—Evelyn Huang
*Attorney, Agent, or Firm*—Millen, White, Zelano & Branigan

[57] ABSTRACT

Novel imidazopyridine derivatives of the formula

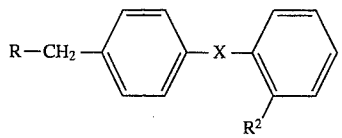

wherein
R is

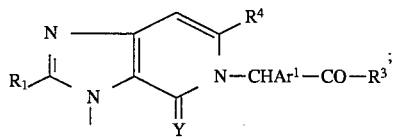

and $R^1$, $R^2$, $R^3$, $R^4$, $Ar^1$, X and Y are as defined in the specification, and their salts, exhibit antagonistic properties toward angiotensin II and can be used for the treatment of hypertension, aldosteronism, cardiac insufficiency and increased intraocular pressure, and of disorders of the central nervous system.

10 Claims, No Drawings

IMIDAZOPYRIDINES

BACKGROUND OF THE INVENTION

The invention relates to novel imidazopyridine derivatives of the formula 1

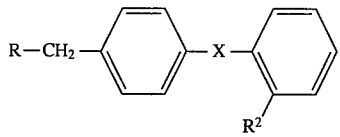

wherein
R is

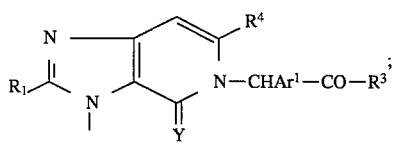

$R^1$ is A, alkenyl or alkynyl each having up to 6 C atoms, $C_3$–$C_7$-cycloalkyl-$C_kH_{2k}$— or $C_1$–$C_6$-alkyl, wherein a $CH_2$ group is replaced by O or S, $R^2$ is H, COOH, COOA, CN, $NO_2$, $NHCOR^5$, $NHSO_2R^5$ or 1H-tetrazol-5-yl, $R^3$ is $NR^6R^7$, O—$C_3$–$C_7$-cycloalkyl, OAr or, if $Ar^1$ is naphthyl, also OH or OA, $R^4$ is H or Hal, $R^5$ is alkyl having 1–5 C atoms, wherein one or more H atoms can also be replaced by F, $R^6$ and $R^7$ are each, independently, H, A, alkenyl or alkynyl each having up to 6 C atoms, $C_3$–$C_7$-cycloalkyl-$C_kH_{2k}$, Ar, $ArC_nH_{2n}$- or Het, $R^6$ is also —$CH_2COOA$, —$SO_2$—A or —$SO_2$—Ar, $R^6$ and $R^7$ together are also an alkylene chain having 2–5 C atoms, which can be monosubstituted or polysubstituted by carbonyl oxygen, A, Ar, Het, —CO—Ar, —COOA, —CO—$N(A)_2$, —$CH_2OH$, —$SO_2$—Ar and/or —NH—CO—A and/or interrupted by O or by —$NR^8$— and/or fused with a benzene ring, $R^8$ is H, A, Ar, CHO, COOA, Het or $SO_2$—Ar, X is absent or is —NH—CO—, —CO—NH—, —O—CH(COOH)—, —NH—CH(COOH)—, —NA—CH(COOH)—, —CH=C(COOH)—, —CH=C(CN)— or —CH=C(1H-tetrazol-5-yl)-, Y is O or S, A is alkyl having 1–6 C atoms, Ar and $Ar^1$ are each unsubstituted phenyl groups or naphthyl groups or phenyl groups or naphthyl groups monosubstituted or disubstituted by $R^5$, $OR^5$, COOH, COOA, CN, $NO_2$, $NH_2$, $NHCOR^5$, $NHSO_2R^5$, Hal or 1H-tetrazol-5-yl, Het is a five- or six-membered heteroaromatic radical having 1 to 3 N, O and/or S atoms, which can also be fused with a benzene or pyridine ring and/or can be monosubstituted or polysubstituted by A, Hal is F, Cl, Br or I, k is 0, 1, 2, 3 or 4, and n is 1, 2, 3, 4, 5 or 6, and their salts.

Similar compounds are known from European Patent Application A2-0 400 974.

An object of the invention is to provide novel compounds with valuable properties, especially compounds which can be used for the preparation of drugs.

Upon further study of the specification and appended claims, further objects and advantages of this invention will become apparent to those skilled in the art.

It has been found that the compounds of the formula I and their salts possess very valuable pharmacological properties coupled with a good tolerance. In particular, they exhibit antagonistic properties toward angiotensin II and can therefore be used as pharmaceutical active ingredients for the prophylaxis and/or therapy of coronary, cardiovascular and vascular disorders, in particular for the treatment of angiotensin II-dependent hypertension, aldosteronism, cardiac insufficiency and increased intraocular pressure, and of disorders of the central nervous system, also of hypertrophy and hyperplasia of the blood vessels and of the heart, angina pectoris, cardiac infarct, stroke, restenoses after angioplasty or by-pass operations, of ischemic peripheral circulatory disorders, arteriosclerosis, glaucomas, macular degeneration, hyperuricemia, kidney function disorders, e.g., kidney failure, diabetic nephropathy, diabetic retinopathy, psoriasis, of gastrointestinal disorders, bladder disorders, pulmonary edema, chronic bronchitis, angiotensin II-mediated disorders in female reproductive organs, perceptive disorders, e.g., dementia, amnesia, memory function disorders, anxiety states, depression, epilepsy, Parkinson's Disease and/or bulimia.

These effects can be determined by conventional in vitro or in vivo methods such as, for example, those described in U.S. Pat. Nos. 4,880,804, 5,036,048 and International patent application 91/14367 and also by A. T. Chiu et al., J. Pharmacol. Exp. Therap., 250:867–874 (1989), and by P. C. Wong et al., ibid., 252:719–725 (1990; in vivo, on rats).

In particular, these compounds have a high affinity for the $AT_1$ and for the $AT_2$ receptor, which can be determined, e.g., on the adrenal medulla of rats according to S. Whitebread et al., Biochem. Biophys. Res. Commun., 163:284–291 (1989) and according to A. T. Chiu et al., Eur. J. Pharmacol., 170:117–118 (1989). The compounds additionally exhibit functional antagonism of the $AT_1$ receptor.

The invention relates to the compounds of the formula I and their salts and to a process for the preparation of these compounds and their salts, characterized in that (a) a compound of the formula II

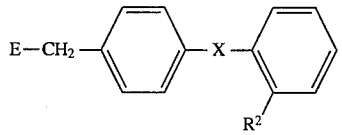

wherein

E is Cl, Br, I, a free OH group or an OH group which has been functionally modified to acquire reactivity, and $R^2$ and X are as defined in formula I, is reacted with a compound of the formula III

H—R   III wherein R is as defined in formula I, or (b) a compound of the formula IV

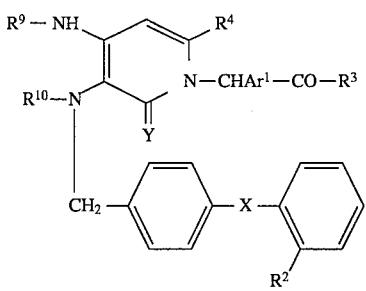

wherein

R⁹ is R¹—CO or H,

R¹⁰ is H (if R⁹ is R¹—CO) or R¹—CO (if R⁹ is H), and

R¹, R², R³, R⁴, X and Y are as defined in formula I, is treated with a cyclizing agent, or (c) to prepare a compound of the formula I wherein X is —NH—CO— or —CO—NH—, a compound of the formula V

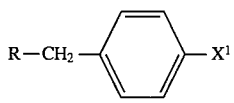

wherein

X¹ is NH₂ or COOH, and

R is as defined in formula I, or a reactive derivative of this compound, is reacted with a compound of the formula VI

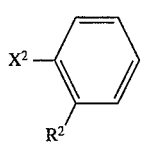

wherein

X² is COOH (if X¹ is NH₂) or NH₂ (if X¹ is COOH), and

R² is as defined in formula I, or with a reactive derivative of this compound, or (d) a compound of the formula VII

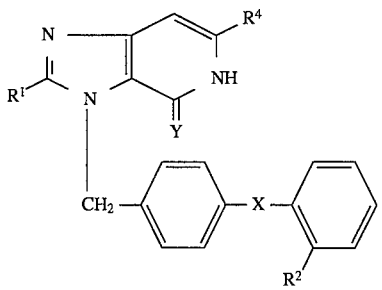

wherein R¹, R², R⁴, X and Y are as defined in formula I, is reacted with a compound of the formula VIII E—CHAr¹—COR³           VIII wherein R³, Ar¹ and E are as defined in formula I, or (e) a carboxylic acid which corresponds to the formula I but instead of the radical R³ contains an OH group (or one of its functional derivatives) is reacted with a compound of the formula H—R³' (wherein R³' is as defined for R³ but is not OH)

or (f) a compound of the formula I is freed from one of its functional derivatives by treatment with a solvolyzing or hydrogenolyzing agent, and/or in that one or more radicals R and/or R² in a compound of the formula I are converted to one or more different radicals R and/or R², and/or a base or acid of the formula I is converted to one of its salts.

Above and below, unless expressly indicated otherwise, the radicals or parameters R, R¹ to R¹⁰, X, Y, A, Ar, Ar¹, Het Hal, k, n, E, X¹ and X² are as defined in formulae I to VI.

In the above formulae, A has 1–6, preferably 1, 2, 3 or 4 C atoms. A is preferably methyl, or else ethyl, propyl, isopropyl, butyl, isobutyl, sec-butyl or tert-butyl, or else pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl. Alkenyl is preferably vinyl, prop-1-enyl, prop-2-enyl or but-1-enyl, or else pent-1-enyl or hex-1-enyl. Alkynyl is preferably ethynyl, prop-1-ynyl or prop-2-ynyl, or else but-1-ynyl, pent-1-ynyl or hex-1-ynyl. If several radicals A, alkenyl or alkynyl are present in a compound of the formula I, they can be identical to or different from one another.

Hal is preferably F, Cl or Br, or else I.

R is a radical derived from 3H-imidazo[4,5-c]pyridine ("3H-IP") or, more precisely, 2-R¹-4-(thi)oxo-5-R³-6-R⁴-4,5-dihydro-3H-imidazo[4,5-c]pyridin-3-yl.

Ar and Ar¹ are preferably unsubstituted or further, as indicated, monosubstituted phenyl; in detail preferably phenyl, o-, m- or p-tolyl, o-, m- or p-ethylphenyl, o-, m- or p-trifluoromethylphenyl, o-, m- or p-methoxyphenyl, o-, m- or p-ethoxyphenyl, o-, m- or p-difluoromethoxyphenyl, o-, m- or p-trifluoromethoxyphenyl, o-, m- or p-carboxyphenyl, o-, m- or p-methoxycarbonylphenyl, o-, m- or p-ethoxycarbonylphenyl, o-, m- or p-cyanophenyl, o-, m- or p-nitrophenyl, o-, m- or p-aminophenyl, o-, m- or p-acetamidophenyl, o-, m- or p-trifluoroacetamidophenyl, o-, m- or p-methylsulfonamidophenyl, o-, m- or p-trifluoromethylsulfonamidophenyl, o-, m- or p-fluorophenyl, o-, m- or p-chlorophenyl, o-, m- or p-bromophenyl, o-, m- or p-(1H-tetrazol-5-yl)phenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dimethoxyphenyl as well as 1- or 2-naphthyl.

Het is preferably furan-2- or -3-yl, thien-2- or -3-yl, pyrrol-1-, -2- or -3-yl, imidazol-1-, -2-, -4- or -5-yl, pyrazol-1-, -3-, -4- or -5-yl, oxazol-2-, -4- or -5-yl, isoxazol-3-, -4- or-5-yl, thiazol-2-, -4- or -5-yl, isothiazol-3-, -4- or -5-yl, pyridin-2-, -3- or -4-yl or pyrimidin-2-, -4-, -5- or -6-yl, or else preferably 1,2,3-triazol-1-, -4- or -5-yl, 1,2,4-triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -4-yl, pyrazinyl, benzofuran-2-, -3-, -4-, -5-, -6- or -7-yl, benzothien-2-, -3-, -4-, -5-, -6- or -7-yl, indol-1-, -2-, -3-, -4-, -5-, -6- or -7-yl, isoindol-1, -2-, -3-, -4-, -5-, -6- or -7-yl, benzimidazol-1-, -2-, -4- or -5-yl, benzopyrazol-1-, -3-, -4-, -5-, -6- or -7-yl, benzoxazol-2-, -4-, -5-, -6- or -7-yl, benzisoxazol-3-, -4-, -5-, -6- or -7-yl, benzothiazol-2-, -4-, -5-, -6- or -7-yl, benzisothiazol-2-, -4-, -5-, -6- or -7-yl, benz-2,1,3-oxadiazol-4-, -5-, -6- or -7-yl, quinolin-2-, -3-, -4-, -5-, -6-, -7- or -8-yl, isoquinolin-1-, -3-, -4-, -5-, -6-, -7- or -8-yl, cinnolin-3-, -4-, -5-, -6-, -7- or -8-yl, quinazolin-2-, -4-, -5-, -6-, -7- or -8-yl, 1H-imidazo[4,5-b]pyridin-1-, -2-, -5-, -6- or -7-yl, 3H-imidazo[4,5-b]pyridin-2-, -3-, -5-, -6- or -7-yl, 1H-imidazo[4,5-c]pyridin-1-, -2-, -4-, -6- or -7-yl or 3H-imidazo[4,5-c]pyridin-2-, -3-, -4-, -6- or -7-yl.

The term "Het" also includes the homologous radicals in which the heteroaromatic ring is substituted by one or more, preferably 1 or 2 groups A, preferably methyl and/or ethyl groups, for example, 3-, 4- or 5-methylfuran-2-yl, 2-, 4- or 5-methylfuran-3-yl, 2,4-dimethylfuran-3-yl, 3-, 4- or 5-methylthien-2-yl, 3-methyl-5-tert-butylthien-2-yl, 2-, 4- or 5-methylthien-3-yl, 2- or 3-methylpyrrol-1-yl, 1-, 3-, 4- or 5-methylpyrrol-2-yl, 3,5-dimethyl-4-ethylpyrrol-2-yl, 2-, 4- or 5-methylimidazol-1-yl, 4-methylpyrazol-5-yl, 4- or 5-methylisoxazol-3-yl, 3- or 5-methylisoxazol-4-yl, 3- or 4-methylisoxazol-5-yl, 3,4-dimethylisoxazol-5-yl, 4- or 5-methylthiazol-2-yl, 4- or 5-ethylthiazol-2-yl, 2- or 5-methylthiazol-4-yl, 2- or 4-methylthiazol-5-yl, 2,4-dimethylthiazol-5-yl, 3-, 4-, 5- or 6-methylpyridin-2-yl, 2-, 4-, 5- or 6-methylpyridin-3-yl, 2- or 3-methylpyridin-4-yl, 4-methylpyrimidin-2-yl, 4,5-dimethylpyrimidin-2-yl, 2-, 5- or 6-methylpyrimidin-4-yl, 2,6-dimethylpyrimidin-4-yl, 3-, 4-, 5-, 6- or 7-methylbenzofuran-2-yl, 2-ethylbenzofuran-3-yl, 3-, 4-, 5-, 6- or 7-methylbenzothien-2-yl, 3-ethylbenzothien-2-yl, 1-, 2-, 4-, 5-, 6- or 7-methylindol-3-yl, 1-methylbenzimidazol-5- or -6-yl or 1-ethylbenzimidazol-5- or -6-yl.

The groups —$C_kH_{2k}$— and —$C_nH_{2n}$— are preferably straight-chain and are thus preferably —$(CH_2)_n$— and —$(CH_2)_k$—, in particular —$CH_2$—, also —$CH_2CH_2$—, —$(CH_2)_3$—, —$(CH_2)_4$—, —$(CH_2)_5$— or —$(CH_2)_6$—, but also, for example, —$CH(CH_3)$—, —$CH_2$—$CH(CH_3)$— or —$C(CH_3)_2$—. The parameter k can preferably also be 0, so that the group —$C_kH_{2k}$— is absent.

The radical $R^1$ is preferably straight-chain and is preferably A, in particular ethyl, propyl or butyl, also methyl, pentyl or hexyl, and also cycloalkyl having 3–7 C atoms, in particular, cyclopropyl, also cyclobutyl, cyclopentyl, cyclohexyl, cycloheptyl, furthermore in particular alkenyl preferably having 3–6 C atoms, in particular allyl or 1-propenyl, also 1-butenyl, 1-pentenyl or 1-hexenyl; alkynyl preferably having 3–6 C atoms, in particular propargyl or 1-propynyl, also 1-butynyl, 1-pentynyl or 1-hexynyl; cycloalkylalkyl preferably having 4–8 C atoms, in particular cyclopropylmethyl, 1- or 2-cyclopropylethyl, also cyclobutylmethyl, cyclopentylmethyl, cyclohexylmethyl; alkoxy preferably having 1–4 C atoms, such as methoxy, ethoxy, propoxy, butoxy, isobutoxy; alkoxyalkyl preferably having 2–5 C atoms, such as methoxymethyl, ethoxymethyl, propoxymethyl, 2-methoxyethyl, 3-methoxypropyl, 2-ethoxyethyl; alkylthio preferably having 1–4 C atoms such as methylthio, ethylthio, propylthio, butylthio, isobutylthio; alkylthioalkyl preferably having 2–5 C atoms such as methylthiomethyl, ethylthiomethyl, propylthiomethyl, 2-methylthioethyl, 3-methylthiopropyl and 2-ethylthioethyl.

The radical $R^2$ is preferably 1H-tetrazol-5-yl, or else preferably COOH, COOCH$_3$, COOC$_2$H$_5$, CN or NHSO$_2$CF$_3$.

The radical $R^3$ is preferably NR$^6$R$^7$, in particular NH$_2$; NHA such as methylamino, ethylamino, propylamino, isopropylamino, butylamino, pentylamino, hexylamino; N(A)$_2$ such as dimethylamino, methylethylamino, diethylamino, dipropylamino, diisopropylamino, dibutylamino; NHAr such as anilino; NAAr such as N-methylanilino, N-ethylanilino, N-propylanilino, N-isopropylanilino, N-butylanilino, N-pentylanilino; bis-cycloalkylalkylamino such as bis(cyclopropylmethyl)amino; unsubstituted alkyleneimino or alkyleneimino substituted as defined, such as aziridino, pyrrolidino, piperidino, 2,6-dimethylpiperidino, 1,2,3,4-tetrahydroquinolino; morpholino; 4-R$^8$-piperazino such as piperazino, 4-A-piperazino, e.g., 4-methylpiperazino, 4-Ar-piperazino, e.g., 4-phenylpiperazino, 4-formylpiperazino, 4-alkoxycarbonylpiperazino, e.g., 4-ethoxycarbonylpiperazino or 4-tert-butoxycarbonylpiperazino. $R^3$ is preferably also O—$C_3$—$C_7$-cycloalkyl such as O-cyclopropyl, O-cyclobutyl, O-cyclopentyl or O-cyclohexyl or O—Ar such as O-phenyl. If Ar$^1$ is naphthyl, $R^3$ can also be OH or OA, e.g., O-methyl, O-ethyl, O-propyl or O-isopropyl.

The radical $R^4$ is preferably H, or else F, Cl, Br or I.

Preferably, the radicals $R^5$ and $R^8$ contain 1, 2 or 3 C atoms and are preferably methyl, ethyl, trifluoromethyl, pentafluoroethyl, 2,2,2-trifluoroethyl or 3,3,3-trifluoropropyl. If a compound of the formula I contains two radicals $R^5$, these can be identical to or different from one another.

The radicals $R^6$ and $R^7$ are preferably H or A, $R^6$ is additionally preferably Ar or Ar—$C_nH_{2n}$.

Further preferred groups —NR$^6$R$^7$ are those in which $R^6$ and $R^7$ together are an alkylene chain having 2–5 C atoms, which can be substituted as indicated and/or interrupted by O or by —NR$^8$—Particularly preferred groups —NR$^6$R$^7$ of this type are, for example, aziridino, pyrrolidino, piperidino, morpholino, piperazino, 2-oxopyrrolidino, 2-alkoxycarbonylpyrrolidino (wherein the alkoxy group contains 1–4 C atoms), such as 2-methoxycarbonylpyrrolidino or 2-ethoxycarbonylpyrrolidino, 2- or 3-alkanoylaminopyrrolidino such as 2- or 3-acetamidopyrrolidino, 2-, 3- or in particular 4-oxopiperidino, 2-, 3- or in particular 4-Ar-piperidino such as 2-, 3- or 4-phenylpiperidino, 4-o-, 4-m- or 4-p-methoxyphenylpiperidino, 4-o-, 4-m- or 4-p-nitrophenylpiperidino, 4-o-, 4-m- or 4-p-chlorophenylpiperidino, 3-hydroxymethyl-4-p-chlorophenylpiperidino, 2-, 3- or 4-(2-thienyl)piperidino, 2-, 3- or 4-N,N-dimethylcarbamoylpiperidino, 2-, 3- or 4-N,N-diethylcarbamoylpiperidino, 2-, 3- or 4-benzoylpiperidino, 2-, 3- or 4-p-methoxybenzoylpiperidino, 4-methylpiperazino, 4-formylpiperazino, 4-phenylpiperazino, 4-o-, 4-m- or 4-p-methoxyphenylpiperazino, 4-o-, 4-m- or 4-p-nitrophenylpiperazino, 4-o-, 4-m- or 4-p-chlorophenylpiperazino, 4-(2-pyrimidinyl)piperazino, 4-methoxycarbonylpiperazino, 4-ethoxycarbonylpiperazino, 4-BOC-piperazino, 4-phenylsulfonylpiperazino, 4-p-tolylsulfonylpiperazino, 4-o-, 4-m- or 4-p-fluorophenylsulfonylpiperazino.

k is preferably 0 or 1.

n is preferably 1, further preferably 2, 3 or 4.

Preferably, the radical X is absent or is —NH—CO— or —CO—NH—.

The radical Y is preferably O, or else S.

The compounds of the formula I can possess one or more chiral centers and can therefore exist in different forms (optically active or optically inactive). Formula I includes all these forms.

Accordingly, the invention relates especially to those compounds of the formula I in which at least one of said radicals has one of the preferred meanings indicated above. Some preferred groups of compounds can be expressed by the following partial formulae Ia to Ii, which correspond to formula I and wherein the radicals not described more precisely are as defined in formula I, except that:

in Ia: X is absent;

in Ib: X is —NH—CO—;

in Ic: X is —CO—NH—;

in Id: X is —O—CH(COOH)—;

in Ie: X is —NH—CH(COOH)—;

in If: X is —CH=C(COOH)—;

in Ig: X is —CH=C(CN)—;

in Ih: X is —CH=C(1H-tetrazol-5-yl)-.

Compounds of the formula Ia are particularly preferred. The following are also preferred:

compounds of the formula Ii to Iai to Ihi, which correspond to the compounds of the formulae I and Ia to Ih, except that in addition Y is an O atom;

compounds of the formulae Ij, Iaj to Iij and Iaij to Ihij, which correspond to formulae I, Ia to Ii and Iai to Ihi, except that in addition $R^4$ is H;

compounds of the formulae Ik, Iak to Ijk, Iaik to Ihik, Iajk to Iijk and Iaijk to Ihijk, which correspond to formulae I, Ia to Ij, Iai to Ihi, Iaj to Iij and Iaij to Ihij, except that in addition $R^2$ is CN or 1H-tetrazol-5-yl.

Among these, preferred compounds are those in which $R^1$ is A or alkenyl each having 2–6, in particular 2, 3 or 4 C atoms or cyclopropyl and/or Ar' is phenyl.

Other preferred groups of compounds have formula I and the other formulae give above, except that the radical $R^3$ is defined as follows:

(a) $NR^6R^7$, (b) $NH_2$, NHA or $N(A)_2$, (c) pyrrolidino, piperidino or morpholino, (d) 4-$R^8$-piperazino, (e) NHAr or NAAr, (f) —O—$C_3$-$C_7$-cycloalkyl.

A small selected group of preferred compounds has formula I wherein $R^1$ is A or cyclopropyl, $R^2$ is 1H-tetrazol-5-yl, $R^3$ is $NH_2$, NHA, $N(A)_2$, NAAr, pyrrolidino, piperidino, morpholino, 4-$R^8$-piperazino or O—$C_3$-$C_7$-cycloalkyl, $R^4$ is H, $R^8$ is A, CHO or COOA, Y is O and Ar and $Ar^1$ are each phenyl and X is absent.

The compounds of the formula I and also the starting materials for their preparation are moreover prepared by methods known per se, such as those described in the literature (for example, in the standard works like Houben-Weyl, Methoden der organischen Chemie (Methods of Organic Chemistry), Georg-Thieme-Verlag, Stuttgart, but especially in European patent application A2-0 400 974 and U.S. Pat. No. 4,880,804), under conditions which are known and suitable for said reactions, it also being possible to make use of variants known per se, which are not mentioned in greater detail here.

If desired, the starting materials can also be formed in situ, so that they are not isolated from the reaction mixture but immediately reacted further to give the compounds of the formula I.

The compounds of the formula I can be obtained by reacting compounds of the formula II with compounds of the formula III. Particularly, the biphenyl derivatives of the formula I (wherein X is absent) are readily obtainable in this way.

In the compounds of the formula II, E is preferably Cl, Br, I or an OH group which has been functionally modified to acquire reactivity, such as alkylsulfonyloxy having 1–6 C atoms (preferably methylsulfonyloxy) or arylsulfonyloxy having 6–10 C atoms (preferably phenyl- or p-tolyl-sulfonyloxy).

The reaction of II with III is conveniently carried out by first converting III to a salt by treatment with a base, for example, with an alkali metal alcoholate such as $CH_3ONa$ or potassium tert-butylate in an alcohol such as methanol or tert-butanol, or with an alkali metal hydride such as NaH, or with an alkali metal alcoholate in dimethylformamide (DMF), and then reacting said salt with II in an inert solvent, for example, an amide such as DMF, N-methylpyrrolidone or dimethylacetamide, or a sulfoxide such as dimethyl sulfoxide (DMSO), conveniently at temperatures of about −20°–100°, preferably of about 10°–30°. Other suitable bases are alkali metal hydrogen carbonates such as $NaHCO_3$ or $KHCO_3$.

The compounds of the formula I can also be obtained by the cyclization of compounds of the formula IV. This cyclization is conveniently carried out by heating with polyphosphoric acid, acetic acid or diglyme to temperatures of about 80°–180°, preferably of about 120°–160°.

Acid amides of the formula I (X=—NH—CO— or —CO—NH—) can also be obtained by reacting compounds of the formula V (or reactive derivatives thereof) with compounds of the formula VI (or reactive derivatives thereof).

Suitable reactive derivatives of the carboxylic acids of the formulae V and VI ($X^1$ or $X^2$=COOH) are advantageously the corresponding chlorides, bromides or anhydrides. The reaction is conveniently carried out in the presence of an inert solvent, for example, a halogenated hydrocarbon such as methylene chloride, chloroform, trichloroethene or 1,2-dichloroethane, or an ether such as tetrahydrofuran (THF) or dioxane, at temperatures of about 0°–150°, preferably of about 20°–80°. If acid halides are reacted, it is recommended to add a base, for example, a tertiary amine such as triethylamine, pyridine or 4-dimethylaminopyridine.

The compounds of the formula I can also be obtained by reacting a compound of the formula VII (corresponding to formula I but with H in place of $CHAr^1$—$COR^3$) with a compound of the formula VIII. This reaction is preferably carried out in an inert solvent, for example, an acid amide such as DMF, N-methylpyrrolidone, 1,3-dimethyl-2-oxo-hexahydropyrimidine or hexamethylphosphorotriamide, an alcohol such as methanol or tert-butanol, an ether such as THF, or a halogenated hydrocarbon such as methylene chloride, or mixtures thereof, as the solvent, and/or in the presence of an alkali metal alcoholate such as sodium methylate or potassium tert-butylate, an alkali metal hydride such as sodium or potassium hydride, an alkali metal carbonate such as sodium or potassium carbonate, an alkali metal bicarbonate such as sodium or potassium bicarbonate, or a tertiary amine such as triethylamine or ethyldiisopropylamine, at temperatures of about −30°–200°, preferably of about 20°–60°.

Compounds of the formula I can also be obtained by reaction of carboxylic acids which correspond to the formula I, but instead of the radical $R^3$ contain an OH group, with compounds of the formula H—R³' (wherein $R^{3'}=R^3$ but is not OH). In this case, the reaction is expediently carried out by customary methods of peptide synthesis, such as are described, for example, in Houben-Weyl, l.c., Volume 15/II, pages 1–806 (1974).

The reaction preferably takes place in the presence of a dehydrating agent, for example, of a carbodiimide such as N,N'-dicyclohexylcarbodiimide ("DCCI"), 1,1'-carbonyldiimidazole or N-3-dimethylaminopropyl-N'-ethylcarbodiimide ("DAPECI"), also propanephosphonic anhydride (cf. Angew. Chem., 92:129 (1980)), diphenylphosphoryl azide or 2-ethoxy-N-ethoxycarbonyl-1,2-dihydroquinoline, in an inert solvent, for example, a halogenated hydrocarbon such as dichloromethane, an ether such as THF or dioxane, an amide such as DMF or dimethylacetamide, a nitrile such as acetonitrile, at temperatures of about −10°–40°, preferably about 0°–30°.

Instead of the carboxylic acids, suitable reactive derivatives of these substances can also be employed in the reaction, for example, those in which reactive groups are intermediately blocked by protective groups. The acids can be used, for example, in the form of their activated esters which are expediently formed in situ, for example, by addition of 1-hydroxybenzotriazole or N-hydroxysuccinimide.

It is also possible to free a compound of the formula I from one of its functional derivatives by solvolysis (for example, hydrolysis) or hydrogenolysis.

Thus, carboxylic acids of the formula I wherein X is —O—CH(COOH), —NH—CH(COOH), —NA—CH(COOH) or —CH═C(COOH) can be obtained by the saponification of corresponding alkyl esters, for example, with NaOH or KOH in aqueous solution, with or without the addition of an inert organic solvent such as methanol, ethanol, THF or dioxane, at temperatures of about 0°–100°, or by the hydrogenolysis of corresponding benzyl esters, for example, on Pd-on-charcoal at pressures of about 1–200 bar and at temperatures of about 0°–100°, in one of the inert solvents indicated.

It is also possible, using one of the methods indicated, to prepare a compound which has formula I but in which a tetrazol-5-yl group is replaced with a 1H(or 2H)-tetrazol-5-yl group functionally modified in the 1-position (or 2-position) (protected by a protecting group). Examples of suitable protecting groups are: triphenylmethyl, which can be cleaved with HCl or formic acid in an inert solvent or solvent mixture, for example, ether/methylene chloride/methanol; 2-cyanoethyl, which can be cleaved with NaOH in water/THF; and p-nitrobenzyl, which can be cleaved with $H_2$/Raney nickel in ethanol (compare European patent application A2-0 291 969).

Some of the starting materials, especially those of the formulae II, VI and VIII, are known. If they are not known, they can be prepared by known methods analogously to known substances. Compounds of the formula III (Y═O) can be obtained for example by reacting carboxylic acids of the formula $R^1$—COOH with 2-E-3,4-diamino-6-$R^4$-pyridines in the presence of polyphosphoric acid; the group E (preferably Cl) is hydrolyzed in the process and compounds of the formula III which carry an H atom in place of the radical —CHAr$^1$—COR$^3$ and are formed initially are then reacted with compounds of the formula VIII.

Compounds of the formula IV can be obtained for example by reacting 1,2-dihydro-2-Y-3,4-diamino-5-$R^4$-pyridines wherein, however, one of the amino groups is protected by an amino-protecting group (for example, benzyl, A—O—CO— or benzyloxycarbonyl), with compounds of the formula II and subsequently cleaving the protecting group and reacting the products with acids of the formula $R^1$—COOH or functional derivatives thereof; they are not normally isolated, but are formed in situ in the last-mentioned reaction.

Compounds of the formula V can be prepared by reacting III with benzyl chlorides of the formula Cl—$CH_2$-p-$C_6H_4$—$X^3$ (wherein $X^3$ is a protected $NH_2$ or COOH group) and subsequently cleaving the protecting group.

Compounds of the formula VII can be obtained for example by reacting compounds of the formula III, carrying an H atom in place of —CHAr$^1$—COR$^3$ with compounds of the formula II.

It is also possible to convert one compound of the formula I to another compound of the formula I by converting one or more of the radicals R and/or $R^2$ to other radicals R and/or $R^2$, for example by reducing nitro groups to amino groups (for example, by hydrogenation on Raney nickel or Pd-on-charcoal in an inert solvent such as methanol or ethanol), and/or functionally modifying free amino and/or hydroxyl groups, and/or freeing functionally modified amino and/or hydroxyl groups by solvolysis or hydrogenolysis, and/or hydrolyzing nitrile groups to COOH groups, or converting nitrile groups to tetrazolyl groups with hydrazoic acid derivatives, for example, sodium azide in N-methylpyrrolidone or trimethyltin azide in toluene, and/or oxidizing thioether groups to SO or $SO_2$ groups, for example, with $H_2O_2$ or a peracid such as 3-chloroperbenzoic acid.

Thus, for example, free amino groups can be acylated in conventional manner with an acid chloride or anhydride, or alkylated with an unsubstituted or substituted alkyl halide, conveniently in an inert solvent such as methylene chloride or THF, and/or in the presence of a base such as triethylamine or pyridine, at temperatures of about −60°–+30°.

If desired, a functionally modified amino and/or hydroxyl group in a compound of the formula I can be freed by solvolysis or hydrogenolysis using conventional methods. Thus, for example, a compound of the formula I containing an NHCOR$^5$ or COOA group can be converted to the corresponding compound of the formula I containing an $NH_2$ or HOOC group instead. COOA groups can be saponified for example with NaOH or KOH in water, water/THF or water/dioxane, at temperatures of about 0°–100°.

The reaction of nitriles of the formula I (for example, those in which $R^2$═CN) with hydrazoic acid derivatives leads to tetrazoles of the formula I (for example, in which $R^2$═1H-tetrazol-5-yl). It is preferable to use trialkyltin azides such as trimethyltin azide, in an inert solvent, for example, an aromatic hydrocarbon such as toluene, at temperatures of about 20°–150°, preferably of about 80°–140°. The trialkyltin group is then eliminated, either by treating with hydrochloric acid, for example, in dioxane, or with alkali, for example, in ethanol/water, or with formic acid, for example, in methanol, or by chromatography on a silica gel column, for example, using ethyl acetate/methanol. The nitriles can also be reacted with sodium azide in N-methylpyrrolidone at temperatures of about 100°–200° to give the tetrazoles.

A base of the formula I can be converted with an acid to the corresponding acid addition salt, for example, by reaction of equivalent amounts of the base and of the acid in an inert solvent such as ethanol and subsequent evaporation. Possible acids for this reaction are especially those which yield physiologically acceptable salts. Thus, it is possible to use inorganic acids, for example, sulfuric acid, nitric acid, hydrohalic acids such as hydrochloric acid or hydrobromic acid, phosphorus acids such as orthophosphoric acid, and sulfamic acid, as well as organic acids, especially aliphatic, alicyclic, araliphatic, aromatic or heterocyclic monobasic or polybasic carboxylic, sulfonic or sulfuric acids, for example, formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-monosulfonic and -disulfonic acids and laurylsulfuric acid. Salts with physiologically unacceptable acids, for example, picrates, can be used for isolating and/or purifying the compound of the formula I.

On the other hand, compounds of the formula I containing COOH or tetrazolyl groups can be converted with bases (for example, sodium or potassium hydroxide or carbonate) to the corresponding metal salts, especially alkali metal or alkaline earth metal salts, or to the corresponding ammonium salts. The potassium salts of the tetrazolyl derivatives are particularly preferred.

The novel compounds of the formula I and their physiologically acceptable salts can be used for the manufacture of pharmaceutical preparations by incorporation into a suitable dosage form together with at least one solid, liquid or semi-liquid excipient or adjunct and, if desired, together with one or more other active ingredients. The resulting formulations can be used as drugs in human or veterinary medicine. Possible excipients are organic or inorganic substances which are suitable for enteral (for example, oral or rectal) or parenteral administration or for administration in the form of an inhalation spray, and which do not react with the novel compounds, examples being water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; lacquered tablets and capsules with coatings or shells resistant to gastric juices are especially of interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant gas mixture. It is convenient here to use the active ingredient in micronized form, it being possible for one or more additional physiologically compatible solvents, for example, ethanol, to be present. Inhalation solutions can be administered with the aid of conventional inhalers. The novel compounds can be lyophilized and the resulting lyophilizates used for example for the manufacture of injectable preparations. The indicated formulations can be sterilized and/or can contain adjuncts such as preservatives, stabilizers and/or wetting agents, emulsifiers, salts for influencing the osmotic pressure, buffer substances and colors and/or flavorings. If desired, they can also contain one or more other active ingredients, for example, one or more vitamins, diuretics or antiphlogistics.

The substances according to the invention are normally administered analogously to other known, commercially available preparations, but in particular analogously to the compounds described in EP-A2 0 400 974, preferably in doses of about 1 mg–1 g, especially of about 50–500 mg per dosage unit. The daily dose is preferably about 0.1–50 mg/kg, especially about 1–10 mg/kg of body weight. However, the particular dose for each individual patient depends on a very wide variety of factors, for example, on the efficacy of the particular compound used, age, body weight, general state of health, sex, diet, time and mode of administration, rate of excretion, drug combination and severity of the particular disease to which the therapy is applied. Oral administration is preferred.

Above and below, all temperatures are given in °C. In the following Examples, "conventional working-up" means: water is added if necessary, the pH is adjusted to about 2–10 if necessary, depending on the constitution of the end product, extraction is carried out with ethyl acetate or methylene chloride and the organic phase is separated off, dried over sodium sulfate, evaporated and purified by chromatography on silica gel and/or by crystallization. FAB= $(M+H)^+$ peak in the mass spectrum, obtained by the fast atom bombardment method.

IP=imidazo[4,5-c]pyridine, IPs=imidazo[4,5-c]pyridines.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 43 41 453.2, filed Dec. 6, 1993, are hereby incorporated by reference.

EXAMPLES

Example 1

(a) A solution of 0.23 g of Na in 20 ml of methanol is added dropwise over 15 minutes to a solution of 3.52 g of 2-butyl-5-(α-N,N-dimethylcarbamoylbenzyl)- 4,5-dihydro-4-oxo-3H-IP [obtainable by condensation of valeric acid with 3,4-diamino-2-chloropyridine, in the presence of polyphosphoric acid, to give 2-butyl-4,5-dihydro-4-oxo-1(or 3)H-IP, reaction with benzyl bromide in methanol, in the presence of $CH_3ONa$, to give 3-benzyl-2-butyl-4,5-dihydro-4-oxo-3H-IP, reaction with α-bromo-N,N-dimethylphenylacetamide in DMF, in the presence of potassium tert-butylate, to give 3-benzyl-2-butyl-5-(α-N,N-dimethylcarbamoylbenzyl)- 4,5-dihydro-4-oxo-3H-IP, and hydrogenolytic cleavage of the benzyl group] in 75 ml of methanol. The mixture is stirred for a further 30 minutes at 20° and evaporated, the residue is dissolved in 20 ml of DMF, and a solution of 3.05 g of methyl 4'-bromomethyl-biphenyl-2-carboxylate (IIa) in 10 ml of DMF is added dropwise at 0°, with stirring. The mixture is stirred for 16 hours at 20°, evaporated, worked up in a conventional manner and chromatographed on silica gel to give 2-butyl-3-(2'-methoxycarbonylbiphenyl- 4-ylmethyl)-4,5-dihydro-4-oxo-5-(α-N,N-dimethylcarbamoylbenzyl)-3H-IP.

(b) A mixture of 1 g of the methyl ester obtained according to (a), 12 ml of 2N aqueous NaOH solution and 48 ml of methanol is boiled for 2 hours and then evaporated. The residue is worked up in a conventional manner (aqueous hydrochloric acid to pH 3/methylene chloride) to give 2-butyl-3-(2'-carboxybiphenyl-4-ylmethyl)-4,5-dihydro-4-oxo- 5-(α-N,N-dimethylcarbamoylbenzyl)-3H-IP.

Example 2

2-Butyl-3-[p-(1-cyano-2-phenylvinyl)benzyl]-4,5-dihydro-4-oxo-5-(α-N,N-dimethylcarbamoylbenzyl)-3H-IP is obtained analogously to Example 1 from 3.52 g of 2-butyl-4,5-dihydro-4-oxo-5-(α-N,N-dimethylcarbamoylbenzyl)-3H-IP and 2.98 g of 3-p-bromomethylphenyl-2-phenylacrylonitrile [m.p. 178°; obtainable by condensation of p-tolylaldehyde with phenylacetonitrile in ethanol, in the presence of $C_2H_5ONa$, to give 2-phenyl-3-p-tolylacrylonitrile (m.p. 61°), and bromination with N-bromosuccinimide in methylene chloride].

Example 3

A mixture of 1.02 g of valeric acid, 5.2 g of 4-amino-1, 2-dihydro-2-oxo- 3-[2'-(1H-tetrazol-5-yl)biphenyl-4-ylmethylamino]-1-(α-N,N-dimethylcarbamoylbenzyl)pyridine

[obtainable by reaction of 3-amino-4-benzylamino-1,2-dihydro-2-oxo-1-(α-N,N-dimethylcarbamoylbenzyl)pyridine with 4-bromomethyl-2'-cyanobiphenyl to give 4-benzylamino-3-(2'-cyanobiphenyl- 4-ylmethylamino)-1,2-dihydro-2-oxo-1-(α-N,N-dimethylcarbamoylbenzyl)pyridine, reaction with trimethyltin azide to give 4-benzylamino-1,2-dihydro-2-oxo-3-(2'-(1H-tetrazol-5-yl)biphenyl-4-ylmethylamino)- 1-(α-N,N-dimethylcarbamoylbenzyl)pyridine, and hydrogenolytic cleavage of the benzyl group] and 50 g of polyphosphoric acid is heated for 5 hours at 140°. 4-Amino-1,2-dihydro-2-oxo- 2-(N-(2'-(1H-tetrazol-5-yl)biphenyl-4-ylmethyl)-N-valerylamino)- 1-(α-N,N-dimethylcarbamoylbenzyl)pyridine and 1,2-dihydro-2-oxo-3-(2'-( 1H-tetrazol-5-yl)biphenyl-4-ylmethylamino)-1-(α-N,N-dimethylcarbamoylbenzyl)- 4-valerylaminopyridine are formed in situ as intermediates. The mixture is cooled, poured onto ice, rendered alkaline with sodium hydroxide solution and worked up in a conventional manner to give 2-butyl-3-(2'-(1H-tetrazol-5-yl)biphenyl-4-ylmethyl)-4,5-dihydro- 4-oxo-5-(α-N,N-dimethylcarbamoylbenzyl)-3H-IP.

Example 4

A mixture of 1.5 g of 3-p-aminobenzyl-2-butyl-4,5-dihydro-5-(α-N,N-dimethylcarbamoylbenzyl)- 4-oxo-3H-IP [obtainable by reaction of 2-butyl-4,5-dihydro-4-oxo-5-(α-N,N-dimethylcarbamoylbenzyl)-3H-IP with p-nitrobenzyl bromide to give 2-butyl-4,5-dihydro-5-(α-N,N-dimethylcarbamoylbenzyl)- 3-p-nitrobenzyl-4-oxo-3H-IP, and subsequent hydrogenation], 0.6 g of phthalic anhydride and 40 ml of CHCl$_3$ is stirred for 16 hours at 20°. The 2-butyl-3-[4-(o-carboxybenzamido)benzyl]- 4,5-dihydro-5-(α-N,N-dimethylcarbamoylbenzyl)-4-oxo-3H-IP which has precipitated out is filtered off.

Example 5

A mixture of 4.57 g of 3-p-aminobenzyl-2-butyl-4,5-dihydro-5- (α-N,N-dimethylcarbamoylbenzyl)-4-oxo-3H-IP, 3 ml of triethylamine, 0.5 g of 4-dimethylaminopyridine and 120 ml of methylene chloride is cooled to 5° and a solution of 2.88 g of o-trifluoromethanesulfonamidobenzoyl chloride in 20 ml of methylene chloride is added dropwise. The mixture is stirred for a further 16 hours at 20°, evaporated and worked up in a conventional manner to give 2-butyl-4,5-dihydro- 5-(α-N,N-dimethylcarbamoylbenzyl)-4-oxo-3-[4-(o-trifluoromethanesulfonamidobenzamido)benzyl]-3H-IP.

Example 6

A mixture of 4.86 g of 2-butyl-3-p-carboxybenzyl-4,5-dihydro- 5-(α-N,N-dimethylcarbamoylbenzyl)-4-oxo-3H-IP, 12 g of thionyl chloride and 35 ml of CHCl$_3$ is boiled for 6 hours and evaporated. The crude acid chloride obtained is freed of thionyl chloride residues by dissolution in toluene several times, followed each time by evaporation, and is dissolved in 80 ml of THF. This solution is added dropwise to a solution of 1.7 g of anthranilic acid and 0.8 g of NaOH in 100 ml of water and the mixture is stirred for 24 hours and acidified to pH 5 with hydrochloric acid. 2-Butyl-3-[p-(2-carboxyanilinocarbonyl)benzyl]- 4,5-dihydro-5-(α-N,N-dimethylcarbamoylbenzyl)-4-oxo-3H-IP is obtained after conventional working-up.

Example 7

(a) 1.25 g of potassium tert-butylate are added at 20° to a solution of 3.82 g of 2-butyl-3-(2'-cyanobiphenyl-4-ylmethyl)-4,5-dihydro- 4-oxo-3H-IP (m.p. 179°–180°; obtainable from 2-butyl-4,5-dihydro- 4-oxo-1(or 3)H-IP with 4'-bromomethyl-2-cyanobiphenyl in DMF, in the presence of K$_2$CO$_3$) in 35 ml of DMF, with stirring. After stirring for 45 minutes, a solution of 2.42 g of α-bromo-N,N-dimethylphenylacetamide in 25 ml of DMF is added dropwise. The mixture is stirred for a further 16 hours at 20° and worked up in a conventional manner to give 2-butyl-3-(2'-cyanobiphenyl-4-ylmethyl)-4, 5-dihydro-4-oxo- 5-(α-N,N-dimethylcarbamoylbenzyl)-3H-IP; FAB 544.

The following 2-butyl- 3-(2'-cyanobiphenyl-4-ylmethyl)-4,5-dihydro- 4-oxo-5-(CHAr$^1$-COR$^3$)-3H-IPs are obtained analogously:

with cyclopentyl α-bromophenylacetate: -5-(α-cyclopentyloxycarbonylbenzyl)-, FAB 585 with cyclohexyl α-bromophenylacetate: -5-(α-cyclohexyloxycarbonylbenzyl)-, FAB 599 with phenyl α-bromophenylacetate: -5-(α-phenoxycarbonylbenzyl)-, FAB 593 with α-bromophenylacetamide: -5-(α-carbamoylbenzyl)-, FAB 516 with α-bromo-N-methylphenylacetamide: -5-(α-N-methylcarbamoylbenzyl)-, FAB 530 with α-bromo-N-ethylphenylacetamide: -5-(α-N-ethylcarbamoylbenzyl)-, FAB 544 with α-bromo-N-propylphenylacetamide: -5-(α-N-propylcarbamoylbenzyl)-, FAB 558 with α-bromo-N-isopropylphenylacetamide: -5-(α-N-isopropylcarbamoylbenzyl)-, FAB 558 with α-bromo-N-pentylphenylacetamide: -5-(α-N-pentylcarbamoylbenzyl)-, FAB 586 with α-bromo-N,N-diethylphenylacetamide: -5-(α-N,N-diethylcarbamoylbenzyl)-, FAB 572 with α-bromo-N,N-dipropylphenylacetamide: -5-(α-N,N-dipropylcarbamoylbenzyl)-, FAB 600 with α-bromo-N,N-diisopropylphenylacetamide: -5-(α-N,N-diisopropylcarbamoylbenzyl)-, FAB 600 with α-bromo-N,N-bis(cyclopropylmethyl)phenylacetamide: -5-(α-N,N-bis(cyclopropylmethyl)carbamoylbenzyl)-, FAB 612 with α-bromo-N-methylphenylacetanilide: -5-(α-N-methyl-N-phenylcarbamoylbenzyl)-, FAB 605 with α-bromo-N-ethylphenylacetanilide: -5-(α-N-ethyl-N-phenylcarbamoylbenzyl)-, FAB 619 with α-bromo-N-pentylphenylacetanilide: -5-(α-N-pentyl-N-phenylcarbamoylbenzyl)-, FAB 661 with α-bromo-N-phenylphenylacetanilide: -5-(α-N,N-diphenylcarbamoylbenzyl)-, FAB 667 with α-bromophenylacetic acid pyrrolidide: -5-(α-pyrrolidinocarbonylbenzyl)-, FAB 559 with α-bromophenylacetic acid piperidide: -5-(α-piperidinocarbonylbenzyl)-, FAB 573 with α-bromophenylacetic acid 2,6-dimethylpiperidide: -5-(α-2,6-dimethylpiperidinocarbonylbenzyl)-, FAB 601 with α-bromophenylacetic acid 1,2,4,5-tetrahydroquinolide: -5-(α-1,2,3,4-tetrahydroquinolinocarbonylbenzyl)-, FAB 621 with α-bromophenylacetic acid morpholide: -5-(α-morpholinocarbonylbenzyl)-, FAB 575 with α-bromophenylacetic acid 4-methylpiperazide: -5-(α-4-methylpiperazinocarbonylbenzyl)-, FAB 588 with α-bromophenylacetic acid 4-formylpiperazide: -5-(α-4-formylpiperazinocarbonylbenzyl)-, FAB 602 with α-bromophenylacetic acid 4-ethoxycarbonylpiperazide: -5-(α-4-ethoxycarbonylpiperazinocarbonylbenzyl)-, FAB 646 with α-bromophenylacetic acid 4-tert-butoxycarbonylpiperazide: -5-(α-4-tert-butoxycarbonylpiperazinocarbonylbenzyl)-, FAB 674 with isopropyl α-bromo-1-naphthylacetate: -5-(α-isopropoxycarbonyl-1-naphthylmethyl)-, FAB 609 with isopropyl α-bromo-2-naphthylacetate: -5-(α-isopropoxycarbonyl-2-naphthylmethyl)-, FAB 609.

(b) A mixture of 5.43 g of the compound obtained according to (a), 20.6 g of trimethyltin azide and 200 ml of toluene is boiled for 24 hours and then evaporated. The residue is taken up in 100 ml of methanolic HCl and the mixture is stirred for 2 hours at 20° and worked up in a conventional manner (saturated NaCl solution/methylene chloride). Chromatography (ethyl acetate/hexane 80:20) gives 2-butyl-3-(2'-(1H-tetrazolyl)biphenyl-4-ylmethyl)-4,5-dihydro-4-oxo- 5-(α-N,N-dimethylcarbamoylbenzyl)-3H-IP; K salt, m.p. 257°.

The following 2-butyl-3-(2'-(1H-tetrazol-5-yl)biphenyl-4-yl-methyl)- 4,5-dihydro-4-oxo-5-(CHAr$^1$—COR$^3$)-3H-IPs (but in the reaction of esters instead of methanol using the alcohol corresponding to the ester as a solvent) are obtained analogously from the 2'-cyanobiphenylyl compounds indicated under (a):

-5-(α-cyclopentyloxycarbonylbenzyl)-, hexahydrate, m.p. 133°
-5-(α-cyclohexyloxycarbonylbenzyl)-, FAB 642
-5-(α-phenoxycarbonylbenzyl)-, FAB 636
-5-(α-carbamoylbenzyl)-, m.p. 274°
-5-(α-N-methylcarbamoylbenzyl)-
-5-(α-N-ethylcarbamoylbenzyl)-
-5-(α-N-propylcarbamoylbenzyl)-
-5-(α-N-isopropylcarbamoylbenzyl)-, K salt, m.p.>300°
-5-(α-N-pentylcarbamoylbenzyl)-
-5-(α-N,N-diethylcarbamoylbenzyl)-, K salt, m.p. 181°
-5-(α-N,N-dipropylcarbamoylbenzyl)-, K salt, m.p. 187°
-5-(α-N,N-diisopropylcarbamoylbenzyl)-, K salt, m.p. 181°
-5-(α-N,N-bis(cyclopropylmethyl)carbamoylbenzyl)-, K salt, m,p. 234°
-5-(α-N-methyl-N-phenylcarbamoylbenzyl)-, K salt, m.p.>300°
-5-(α-N-ethyl-N-phenylcarbamoylbenzyl)-, K salt, m.p. 180°
-5-(α-N-pentyl-N-phenylcarbamoylbenzyl)-, m.p. 101°
-5-(α-N,N-diphenylcarbamoylbenzyl)-, K salt, m,p. 238°
-5-(α-pyrrolidinocarbonylbenzyl)-, K salt, m.p. 183°
-5-(α-piperidinocarbonylbenzyl)-, K salt, m.p. 201°
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-, K salt, m.p. 195°
-5-(α-4-methylpiperazinocarbonylbenzyl)-
-5-(α-4-formylpiperazinocarbonylbenzyl)-
-5-(α-4-ethoxycarbonylpiperazinocarbonylbenzyl)-
-5-(α-4-tert-butoxycarbonylpiperazinocarbonylbenzyl)-
-5-(α-isopropoxycarbonyl-1-naphthylmethyl)-
-5-(α-isopropoxycarbonyl-2-naphthylmethyl)-.

Example 8

(a) The 2-ethyl-3-(2'-cyanobiphenyl-4-ylmethyl-4,5-dihydro-4-oxo- 5-(CHAr$^1$—COR$^3$)-3H-IPs below are obtained analogously to Example 7(a) from 2-ethyl-3-(2'-cyanobiphenyl-4-ylmethyl)-4,5-dihydro-4-oxo- 3H-IP (m.p. 230°; obtainable from 2-ethyl-4,5-dihydro-4-oxo-1(or 3)H-IP with 4'-bromomethyl-2-cyanobiphenyl) and the compounds of the formula E-CHAr$^1$—COR$^3$ indicated in Example 7(a):

-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-
-5-(α-N-isopropylcarbamoylbenzyl)-
-5-(α-N-pentylcarbamoylbenzyl)-, FAB 558
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-
-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-
-5-(α-N,N-diphenylcarbamoylbenzyl)
-5-(α-pyrrolidinocarbonylbenzyl)-
-5-(α-piperidinocarbonylbenzyl)-, FAB 545
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-
-5-(α-4-methylpiperazinocarbonylbenzyl)-
-5-(α-4-formylpiperazinocarbonylbenzyl)-
-5-(α-4-ethoxycarbonylpiperazinocarbonylbenzyl)-
-5-(α-4-tert-butoxycarbonylpiperazinocarbonylbenzyl)-
-5-(α-isopropoxycarbonyl-1-naphthylmethyl)-
-5-(α-isopropoxycarbonyl-2-naphthylmethyl)-.

(b) The 2-ethyl-3-(2'-(1H-tetrazol-5-yl)biphenyl-4-ylmethyl)- 4,5-dihydro-4-oxo-5-(CHAr$^1$—COR$^3$)-3H-IPs below are obtained analogously to Example 7(b) from the 2'-cyanobiphenylyl compounds indicated under (a):

-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-
-5-(α-N-isopropylcarbamoylbenzyl)-
-5-(α-N-pentylcarbamoylbenzyl)-, K salt, m.p.>300°
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-
-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-
-5-(α-N,N-diphenylcarbamoylbenzyl)-
-5-(α-pyrrolidinocarbonylbenzyl)-
-5-(α-piperidinocarbonylbenzyl)-, K salt, hemipentahydrate, m.p. 215°
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-
-5-(α-4-methylpiperazinocarbonylbenzyl)-
-5-(α-4-formylpiperazinocarbonylbenzyl)-
-5-(α-4-ethoxycarbonylpiperazinocarbonylbenzyl)-
-5-(α-4-tert-butoxycarbonylpiperazinocarbonylbenzyl)-
-5-(α-isopropoxycarbonyl-1-naphthylmethyl)-
-5-(α-isopropoxycarbonyl-2-naphthylmethyl)-.

Example 9

(a) The 2-propyl-3-(2'-cyanobiphenyl-4-ylmethyl)-4,5-dihydro-4-oxo-5-(CHAr$^1$—COR$^3$)-3H-IPs below are obtained analogously to Example 7(a) from 2-propyl-3-(2'-cyanobiphenylyl-4-methyl)-4,5-dihydro-4-oxo-3H-IP (obtainable from 2-propyl-4,5-dihydro-4-oxo-1(or 3)H-IP with 4'-bromomethyl-2-cyanobiphenyl) and the compounds of the formula E—CHAr$^1$—COR$^3$ indicated in Example 7(a):
-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-
-5-(α-N-isopropylcarbamoylbenzyl)-
-5-(α-N-pentylcarbamoylbenzyl)-
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-
-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-
-5-(α-N,N-diphenylcarbamoylbenzyl)-
-5-(α-pyrrolidinocarbonylbenzyl)-
-5-(α-piperidinocarbonylbenzyl)-
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-, FAB 561
-5-(α-4-methylpiperazinocarbonylbenzyl)-, FAB 574
-5-(α-4-formylpiperazinocarbonylbenzyl)-, FAB 588
-5-(α-4-ethoxycarbonylpiperazinocarbonylbenzyl)-, FAB 632
-5-(α-4-tert-butoxycarbonylpiperazinocarbonylbenzyl)-, FAB 660
-5-(α-isopropoxycarbonyl-1-naphthylmethyl)-, FAB 595
-5-(α-isopropoxycarbonyl-2-naphthylmethyl)-, FAB 595.

(b) The 2-propyl-3-(2'-(1H-tetrazol-5-yl)biphenyl-4-ylmethyl)- 4,5-dihydro-4-oxo-5-(CHAr$^1$—COR$^3$)-3H-IPs below are obtained analogously to Example 7(b) from the 2'-cyanobiphenylyl compounds indicated under (a):
-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-
-5-(α-N-isopropylcarbamoylbenzyl)-
-5-(α-N-pentylcarbamoylbenzyl)-
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-
-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-
-5-(α-N,N-diphenylcarbamoylbenzyl)-
-5-(α-pyrrolidinocarbonylbenzyl)-
-5-(α-piperidinocarbonylbenzyl)-
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-
-5-(α-4-methylpiperazinocarbonylbenzyl)-, K salt, m.p.>300°
-5-(α-4-formylpiperazinocarbonylbenzyl)-, K salt, m.p. 259°
-5-(α-4-ethoxycarbonylpiperazinocarbonylbenzyl)-, K salt, m.p. 297°
-5-(α-4-tert-butoxycarbonylpiperazinocarbonylbenzyl)-, K salt, m.p. 218°
-5-(α-isopropoxycarbonyl-1-naphthylmethyl)-, m.p. 197°
-5-(α-isopropoxycarbonyl-2-naphthylmethyl)-, m.p. 206°.

Example 10

(a) The 2-cyclopropyl-3-(2'-cyanobiphenyl-4-ylmethyl)-4,5-dihydro- 4-oxo-5-(CHAr$^1$—COR$^3$)-3H-IPs below are obtained analogously to Example 7(a) from 2-cyclopropyl-3-(2'-cyanobiphenyl-4-ylmethyl)- 4,5-dihydro-4-oxo-3H-IP (m.p. 183°; obtainable from 2-cyclopropyl- 4,5-dihydro-4-oxo-1(or 3)H-IP with 4'-bromomethyl-2-cyanobiphenyl) and the compounds of the formula E—CHAr$^1$—COR$^3$ indicated in Example 7(a):
-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-, FAB 542
-5-(α-N-isopropylcarbamoylbenzyl)-
-5-(α-N-pentylcarbamoylbenzyl)-
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-
-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-
-5-(α-N,N-diphenylcarbamoylbenzyl)-
-5-(α-pyrrolidinocarbonylbenzyl)-
-5-(α-piperidinocarbonylbenzyl)-
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-
-5-(α-4-methylpiperazinocarbonylbenzyl)-
-5-(α-4-formylpiperazinocarbonylbenzyl)-
-5-(α-4-ethoxycarbonylpiperazinocarbonylbenzyl)-
-5-(α-4-tert-butoxycarbonylpiperazinocarbonylbenzyl)-
-5-(α-isopropoxycarbonyl-1-naphthylmethyl)-
-5-(α-isopropoxycarbonyl-2-naphthylmethyl)-.

(b) The 2-cyclopropyl-3-(2'-(1H-tetrazol-5-yl)biphenyl-4-yl-methyl)- 4,5-dihydro-4-oxo-5-(CHAr$^1$—COR$^3$)-3H-IPs below are obtained analogously to Example 7(b) from the 2'-cyanobiphenylyl compounds indicated under (a):
-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-, nonahydrate, FAB 585
-5-(α-N-isopropylcarbamoylbenzyl)-
-5-(α-N-pentylcarbamoylbenzyl)-
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-
-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-

-5-(α-N,N-diphenylcarbamoylbenzyl)-
-5-(α-pyrrolidinocarbonylbenzyl)-
-5-(α-piperidinocarbonylbenzyl)-
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-
-5-(α-4-methylpiperazinocarbonylbenzyl)-
-5-(α-4-formylpiperazinocarbonylbenzyl)-
-5-(α-4-ethoxycarbonylpiperazinocarbonylbenzyl)-
-5-(α-4-tert-butoxycarbonylpiperazinocarbonylbenzyl)-
-5-(α-isopropoxycarbonyl-1-naphthylmethyl)-
-5-(α-isopropoxycarbonyl-2-naphthylmethyl)-.

Example 11

(a) 2-Butyl-3-(2'-(2-triphenylmethyl-2H-tetrazol-5-yl)biphenyl-4-ylmethyl)-4,5-dihydro-4-oxo-5-(α-N,N-dimethylcarbamoylbenzyl)-3H-IP is obtained analogously to Example 7(a) from 2-butyl-3-(2'-(2-triphenylmethyl-2H-tetrazol-5-yl)biphenyl-4-ylmethyl)-4,5-dihydro-4-oxo-3H-IP using α-bromo-N,N-dimethylphenylacetamide.

The 2-butyl-3-(2'-(2-triphenylmethyl-2H-tetrazol-5-yl)biphenyl-4-ylmethyl)- 4,5-dihydro-4-oxo-5-(CHAr$^1$—COR$^3$)-3H-IPs below:
-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-
-5-(α-N-isopropylcarbamoylbenzyl)-
-5-(α-N-pentylcarbamoylbenzyl)-
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-
-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-
-5-(α-N,N-diphenylcarbamoylbenzyl)-
-5-(α-pyrrolidinocarbonylbenzyl)-
-5-(α-piperidinocarbonylbenzyl)-
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-
-5-(α-4-methylpiperazinocarbonylbenzyl)-
-5-(α-4-formylpiperazinocarbonylbenzyl)-
-5-(α-4-ethoxycarbonylpiperazinocarbonylbenzyl)-
-5-(α-4-tert-butoxycarbonylpiperazinocarbonylbenzyl)-
-5-(α-isopropoxycarbonyl-1-naphthylmethyl)-
-5-(α-isopropoxycarbonyl-2-naphthylmethyl)-;

the 2-ethyl-3-(2'-(2-triphenylmethyl-2H-tetrazol-5-yl)biphenyl-4-ylmethyl)- 4,5-dihydro-4-oxo-5-(CHAr$^1$—COR$^3$)-3H-IPs below:
-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-
-5-(α-N-isopropylcarbamoylbenzyl)-
-5-(α-N-pentylcarbamoylbenzyl)-
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-
-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-
-5-(α-N,N-diphenylcarbamoylbenzyl)-
-5-(α-pyrrolidinocarbonylbenzyl)-
-5-(α-piperidinocarbonylbenzyl)-
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-
-5-(α-4-methylpiperazinocarbonylbenzyl)-
-5-(α-4-formylpiperazinocarbonylbenzyl)-
-5-(α-4-ethoxycarbonylpiperazinocarbonylbenzyl)-
-5-(α-4-tert-butoxycarbonylpiperazinocarbonylbenzyl)-
-5-(α-isopropoxycarbonyl-1-naphthylmethyl)-
-5-(α-isopropoxycarbonyl-2-naphthylmethyl)-;

the 2-propyl-3-(2'-(2-triphenylmethyl-2H-tetrazol-5-yl)biphenyl-4-ylmethyl)-4,5-dihydro-4-oxo-5-(CHAr$^1$—COR$^3$)-3H-IPs below:
-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-
-5-(α-N-isopropylcarbamoylbenzyl)-
-5-(α-N-pentylcarbamoylbenzyl)-
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-
-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-
-5-(α-N,N-diphenylcarbamoylbenzyl)-
-5-(α-pyrrolidinocarbonylbenzyl)-
-5-(α-piperidinocarbonylbenzyl)-
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-
-5-(α-4-methylpiperazinocarbonylbenzyl)-
-5-(α-4-formylpiperazinocarbonylbenzyl)-
-5-(α-ethoxycarbonylpiperazinocarbonylbenzyl)-
-5-(α-4-tert-butoxycarbonylpiperazinocarbonylbenzyl)-
-5-(α-isopropoxycarbonyl-1-naphthylmethyl)-
-5-(α-isopropoxycarbonyl-2-naphthylmethyl)-;

and the 2-cyclopropyl-3-(2'-(2-triphenylmethyl-2H-tetrazol-5-yl)-biphenyl- 4-ylmethyl)-4,5-dihydro-4-oxo-5-(CHAr$^1$—COR$^3$-3H-IPs below:
-5-(α-cyclopentyloxycarbonylbenzyl)-
-5-(α-cyclohexyloxycarbonylbenzyl)-
-5-(α-phenoxycarbonylbenzyl)-
-5-(α-carbamoylbenzyl)-
-5-(α-N-methylcarbamoylbenzyl)-
-5-(α-N-ethylcarbamoylbenzyl)-
-5-(α-N-propylcarbamoylbenzyl)-
-5-(α-N-isopropylcarbamoylbenzyl)-
-5-(α-N-pentylcarbamoylbenzyl)-
-5-(α-N,N-dimethylcarbamoylbenzyl)-
-5-(α-N,N-diethylcarbamoylbenzyl)-
-5-(α-N,N-dipropylcarbamoylbenzyl)-
-5-(α-N,N-diisopropylcarbamoylbenzyl)-
-5-(α-N,N-bis(cyclopropylmethyl)carbamoylbenzyl)-

-5-(α-N-methyl-N-phenylcarbamoylbenzyl)-
-5-(α-N-ethyl-N-phenylcarbamoylbenzyl)-
-5-(α-N-pentyl-N-phenylcarbamoylbenzyl)-
-5-(α-N,N-diphenylcarbamoylbenzyl)-
-5-(α-pyrrolidinocarbonylbenzyl)-
-5-(α-piperidinocarbonylbenzyl)-
-5-(α-2,6-dimethylpiperidinocarbonylbenzyl)-
-5-(α-1,2,3,4-tetrahydroquinolinocarbonylbenzyl)-
-5-(α-morpholinocarbonylbenzyl)-
-5-(α-4-methylpiperazinocarbonylbenzyl)-
-5-(α-4-formylpiperazinocarbonylbenzyl)-
-5-(α-4-ethoxycarbonylpiperazinocarbonylbenzyl)-
-5-(α-4-tert-butoxycarbonylpiperazinocarbonylbenzyl)-
-5-(α-isopropoxycarbonyl-1-naphthylmethyl)-
-5-(α-isopropoxycarbonyl-2-naphthylmethyl)-;

are obtained analogously using the compounds of the formula E—$R^{3'}$ indicated in Example 7(a).

(b) The product obtained according to (a) (1 g) is dissolved in 60 ml of 4N HCl in dioxane and the solution is stirred for 16 hours at 20°. It is evaporated and worked up in a conventional manner to give 2-butyl-3-(2'-(1H-tetrazol-5-yl)biphenyl-4-ylmethyl)-4,5-dihydro- 4-oxo-5-(α-N,N-dimethylcarbamoylbenzyl)-3H-IP; K salt, m.p. 257°.

The 1H-tetrazol-5-yl compounds indicated in Examples 7(b), 8(b), 9(b) and 10(b) are obtained analogously from the corresponding 2-triphenylmethyl-2H-tetrazol-5-yl compounds indicated under (a).

Example 12

2-Butyl-3-(p-2-cyano-2-phenylvinylbenzyl)-4,5-dihydro-5-(α-N,N-dimethylcarbamoylbenzyl)- 4-oxo-3H-IP is obtained analogously to Example 7(a) from 2-butyl-3-(p-2-cyano-2-phenylvinylbenzyl)-4,5-dihydro- 4-oxo-3H-IP (m.p. 160°; obtainable from 2-butyl-4,5-dihydro- 4-oxo-1(or 3)H-IP and 3-p-bromomethylphenyl-2-phenylacrylonitrile) with α-bromo-N,N-dimethylphenylacetamide.

Example 13

210 mg of DCCl are added to a solution of 0.52 g of 2-butyl-3-( 2'-cyanobiphenyl-4-ylmethyl)-4,5-dihydro-4-oxo-5-(α-carboxybenzyl)- 3H-IP ("B"; obtainable by reaction of 2-butyl-3-(2'-cyanobiphenyl-4-ylmethyl)- 4,5-dihydro-4-oxo-3H-IP with ethyl α-bromophenylacetate and subsequent hydrolysis) in 14 ml of THF, the mixture is stirred at 20° for 10 min, 72 mg of pyrrolidine are added and the mixture is stirred at 20° for a further 18 hours. It is filtered, the filtrate is worked up in the customary manner, the crude product is chromatographed on silica gel (ethyl acetate/methanol 80:20) and 2-butyl-3-( 2'-cyanobiphenyl-4-ylmethyl)-4,5-dihydro-4-oxo-5-(α-pyrrolidinocarbonylbenzyl)- 3H-IP, FAB 559, is obtained.

Example 14

(a) The 2-butyl-3-(2'-cyanobiphenyl-4-ylmethyl)-4,5-dihydro-4-oxo- 5-(CHAr$^1$—COR$^3$)-3H-IPs below are obtained analogously to Example 7(a):
with α-bromo-N-ethyl-N-isopropyl-phenylacetamide:
  -5-(α-N-ethyl-N-isopropylcarbamoylbenzyl)-, FAB 586
with α-bromo-phenylacetic acid-(2-phenylpiperidide);
  -5-(α-2-phenylpiperidinocarbonylbenzyl)-, FAB 660
with 2-(α-bromophenylacetyl)-1,2,3,4-tetrahydroisoquinoline:       -5-(α-1,2,3,4-tetrahydroisoquinolinocarbonylbenzyl)-, FAB 621
with α-bromo-N-methylsulfonylphenylacetamide: -5-(α-N-methylsulfonylcarbamoylbenzyl)-, FAB 637
with α-bromo-N-phenylsulfonylphenylacetamide: -5-(α-N-phenylsulfonylcarbamoylbenzyl)-, FAB 699.

(b) the 2-butyl-3-(2'-(1H-5-tetrazolyl)-biphenyl-4-ylmethyl)- 4,5-dihydro-4-oxo-5-(CHAr$^1$—COR$^3$)-3H-IPs below are obtained analogously to Example 7(b) from the 2'-cyanobiphenylyl compounds indicated under (a):
-5-(α-N-ethyl-N-isopropylcarbamoylbenzyl)-, K salt, FAB 667
-5-(α-2-phenylpiperidinocarbonylbenzyl)-, K salt, FAB 741
-5-(α-1,2,3,4-tetrahydroisoquinolinocarbonylbenzyl)-, K salt, FAB 713
-5-(α-N-methylsulfonylcarbamoylbenzyl)-, FAB 637
-5-(α-N-phenylsulfonylcarbamoylbenzyl)-, FAB 699.

The following examples relate to pharmaceutical formulations containing active ingredients of the formula I or their salts.

Example A

Tablets and Coated Tablets

Tablets of the following composition are produced by compression in a conventional manner and, where required, are provided with a conventional sucrose-based coating:

| | |
|---|---|
| Active ingredient of the formula I | 100 mg |
| Microcrystalline cellulose | 278.8 mg |
| Lactose | 110 mg |
| Maize starch | 11 mg |
| Magnesium stearate | 5 mg |
| Finely divided silicon dioxide | 0.2 mg |

Example B

Hard Gelatin Capsules

Conventional two-part hard gelatin capsules are each filled with

| | |
|---|---|
| Active ingredient of the formula I | 100 mg |
| Lactose | 150 mg |
| Cellulose | 50 mg |
| Magnesium stearate | 6 mg |

Example C

Soft Gelatin Capsules

Conventional soft gelatin capsules are filled with a mixture of mg of active ingredient and 250 mg of olive oil in each case.

Example D

Ampoules

A solution of 200 g of active ingredient in 2 kg of propane-1,2-diol is made up to 10 l with water and filled into ampoules so that each ampoule contains 20 mg of active ingredient.

Example E

Aqueous Suspension for Oral Administration

An aqueous suspension of the active ingredient is prepared in a conventional manner. The unit dose (5 ml) contains 100 mg of active ingredient, 100 mg of Na carboxymethylcellulose, 5 mg of Na benzoate and 100 mg of sorbitol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazopyridine derivative of formula I

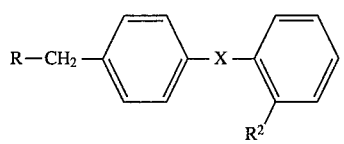

I wherein

R is

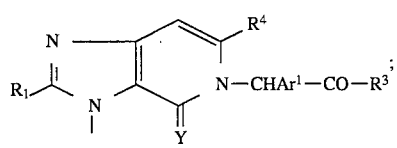

$R^1$ is A, $C_{1-6}$-alkenyl or -alkynyl, $C_{3-7}$-cycloalkyl-$C_kH_{2k}$—, or $C_{1-6}$-alkyl wherein a $CH_2$ group is replaced by O or S;

$R^2$ is H, COOH, COOA, CN, $NO_2$, $NHCOR^5$, $NHSO_2R^5$ or 1H-tetrazol-5-yl;

$R^3$ is $NR^6R^7$, O—$C_{3-7}$-cycloalkyl, OAr or, when $Ar^1$ is naphthyl, also OH or OA;

$R^4$ is H or Hal;

$R^5$ is $C_{1-5}$-alkyl wherein, optionally, one or more H atoms is replaced by F;

$R^6$ and $R^7$ are each, independently, H, A, $C_{1-6}$-alkenyl or -alkynyl, $C_{3-7}$-cycloalkyl-$C_kH_{2k}$, Ar, $ArC_nH_{2n}$— or Het, $R^6$ is also —$CH_2COOA$, —$SO_2$—A or —$SO_2$—Ar, or $R^6$ and $R^7$ together are $C_{2-5}$-alkylene optionally mono- or polysubstituted by one or more of carbonyl oxygen, A, Ar, Het, —CO—Ar, —COOA, —CO—$N(A)_2$, —$CH_2OH$, —$SO_2$—Ar and —NH—CO—A, and optionally interrupted by O or by —$NR^8$— and optionally fused with a benzene ring;

$R^8$ is H, A, Ar, CHO, COOA, Het or $SO_2$—Ar;

X is absent or is —NH—CO—, —CO—NH—, —O—CH(COOH)—, —NH—CH(COOH)—, —NA—CH(COOH)—, —CH=C(COOH)—, —CH=C(CN)— or —CH=C(1H-tetrazol-5-yl)—;

Y is O or S;

A is $C_{1-6}$-alkyl;

Ar and $Ar^1$ are each, independently, phenyl groups or naphthyl groups optionally mono- or disubstituted by $R^5$, $OR^5$, COOH, COOA, CN, $NO_2$, $NH_2$, $NHCOR^5$, $NHSO_2R^5$, Hal or 1H-tetrazol-5-yl;

Het is a five- or six-membered heteroaromatic radical having 1 to 3N, O and/or S atoms, optionally fused with a benzene or pyridine ring and optionally can be mono- or poly-substituted by A;

Hal is F, Cl, Br or I;

k is 0, 1, 2, 3 or 4; and n is 1, 2, 3, 4, 5 or 6, or a salt thereof.

2. An imidazopyridine derivative of claim 1, which is 2-butyl- 3-(2'-(1H-tetrazol-5-yl)biphenyl-4-ylmethyl)-4,5-dihydro-4-oxo-5-(α-N,N-diethylcarbamoylbenzyl)-3H-imidazo[4,5-c]pyridine.

3. A pharmaceutical preparation comprising a compound of claim 1 or a physiologically acceptable salt thereof, and a pharmaceutically acceptable excipient.

4. A preparation of claim 3, wherein said compound is present in an amount of 1 mg–1 g.

5. A method of treating angiotensin(II)-dependent hypertension, comprising administering an effective amount of a compound of claim 1.

6. A method of treating angiotensin(II)-dependent aldosteronism comprising administering an effective amount of a compound of claim 1.

7. A method of treating angiotensin(II)-dependent cardiac insufficiency comprising administering an effective amount of a compound of claim 1.

8. A method of treating angiotensin(II)-dependent elevated intraocular pressure comprising administering an effective amount of a compound of claim 1.

9. A method of treating angiotensin(II)-dependent diseases or disorders comprising administering to a patient in need thereof an effective amount of a compound of claim 1.

10. A method of claim 9, wherein said compound is administered in a daily dosage of 0.1–50 mg/kg of body weight.

* * * * *